US00PP14364P29

(12) United States Plant Patent
Slaughter et al.

(10) Patent No.: US PP14,364 P2
(45) Date of Patent: Dec. 9, 2003

(54) PEACH TREE NAMED 'BURPEACHSIXTEEN'

(50) Latin Name: *Prunus persica*
Varietal Denomination: Burpeachsixteen

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/341,749

(22) Filed: Jan. 13, 2003

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of peach tree (*Prunus persica*), denominated varietally as 'Burpeachsixteen', and which produces an attractively colored yellow-fleshed, clingstone peach which is mature for harvesting and shipment approximately June 8 to June 15 under ecological conditions prevailing in the San Joaquin Valley of central California.

1 Drawing Sheet

BACKGROUND OF THE NEW VARIETY

The present invention relates to a new, novel and distinct variety of peach tree, *Prunus persica,* and which has been denominated varietally as 'Burpeachsixteen'.

ORIGIN

The present variety of peach tree resulted from an on-going program of fruit and nut tree breeding. The purpose of this program is to improve the commercial quality of deciduous fruit and nut varieties, and rootstocks, by creating and releasing promising selections of prunus, malus and regia species. To this end we make both controlled and hybrid cross pollinations each year in order to produce seedling populations from which improved progenies are evaluated and selected.

The seedling 'Burpeachsixteen' was originated by us from a population of open pollinated seedlings grown in our experimental orchards located near Fowler, Calif. These open pollinated seedlings, grown on their own roots, were derived from the 'A25.046' peach tree (unpatented) which was also growing at the same experimental orchard. One seedling, which is the present variety, exhibited especially desirable characteristics, and was designated as 'E4.073.' This desirable seedling was marked for subsequent observation. In 1998, following the fruiting season, the new variety was selected for advanced evaluation and repropagation.

ASEXUAL REPRODUCTION

Asexual reproduction of the new and distinct variety of peach tree was accomplished by budding to 'Nemaguard' Rootstock (unpatented). This was performed by us in our experimental orchard located near Fowler, Calif. Subsequent evaluations performed in later years have shown those asexual reproductions run true to the original tree. All characteristics of the original tree and its fruit were established and appear to be transmitted through succeeding asexual propagations.

SUMMARY OF THE VARIETY

'Burpeachsixteen' is a new and distinct variety of peach tree, which is of large size, and which has vigorous growth, and which further is a regular and productive bearer of relatively large, firm, yellow fleshed, clingstone fruit having a good flavor and eating quality. The new peach tree has a medium chilling requirement of approximately 650 hours. Further, the tree also produces relatively uniformly sized fruit throughout the entire tree. The fruit of the new variety further has a high degree of red skin coloration, and a firm flesh. The fruit also appears to have good handling and shipping qualities. Yet further, the 'Burpeachsixteen' peach tree bears fruit which are ripe for commercial harvesting and shipment on approximately June 8 to 15 under the ecological conditions prevailing in the San Joaquin Valley of Central California. In relative comparison to the 'A25.046' peach tree, the new variety ripens about 10 or more days earlier under the same ecological conditions.

BRIEF DESCRIPTION OF THE DRAWING

The accompanying drawing, which is provided, is a color photograph of the present variety. It depicts two whole mature fruit, and one fruit dissected substantially along the equatorial plane to expose the flesh and the pit thereof. Additionally a characteristic twig bearing typical leaves is shown. Further, a pit has been provided with the flesh removed to reveal its characteristic shape. The external coloration of the fruit as shown is sufficiently matured for harvesting and shipment. The colors are as nearly true as is reasonably possible in a color representation of this type. Due to chemical development, processing and printing, the color of the leaves and fruit depicted in these photographs may or may not be accurate when compared to the actual specimen. For this reason, future color references should be made to the color plates (Royal Horticultural Society) and the other descriptions provided hereinafter.

DETAILED DESCRIPTION

Referring more specifically to the pomological details of this new and distinct variety of peach tree, the following has been observed in the fourth fruiting season under the ecological conditions prevailing at our orchard which is located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally — Considered medium-large when compared to other common commercial peach cultivars ripening in the early season of maturity. The tree of the present variety was pruned to a height of approximately 290.0 cm to about 330.0 cm at maturity.

*Vigor.*—Moderately vigorous. The present variety grew from about 133.0 cm to about 142.0 cm in height during the first growing season. The variety was pruned to a height of approximately 128.6 cm in the first dormant season and primary scaffolds were then selected for the desired tree structure.

*Productivity.*—Productive. Fruit set varies from about twice to several times more than the desired crop load. Fruit set is spaced by thinning to develop the remaining fruit into the desired market size. The number of the fruit set varies with climatic conditions and cultural practices employed during the blooming period and is therefore not distinctive of the variety.

*Bearer.*—Regularity of Bearing. Fruit set has been observed as heavy, and thinning was necessary during the past 5 years.

*Form.*—Upright, and pruned to a vase shape.

*Density.*—Medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements are approximately 650 hours below 7.0 degrees C. The variety appears to be hardy under typical central San Joaquin valley climatic conditions.

Trunk:

*Diameter.*—Approximately 13.1 cm in diameter when measured at a distance of approximately 15.24 cm above the soil level, at the end of the fifth growing season.

*Bark texture.*—Considered moderately rough, with numerous folds of papery scarfskin being present.

*Lenticels.*—Numerous flat, oval lenticels are present. The lenticels range in size in size from approximately 5.0 to 6.0 millimeters in width, and from 1.0 to 2.0 millimeters in height.

*Lenticel color.*—Considered an Orange Brown, (RHS Greyed Orange Group N172 B).

*Bark coloration.*—Variable, but it is generally considered to be grey-brown, (RHS Greyed Orange Group 177 A).

Branches:

*Size.*—Considered medium for the variety.

*Diameter.*—Average as compared to other varieties. The branches have a diameter of about 7.0 centimeters when measured during the fifth year following grafting.

*Surface texture.*—Average, and appearing furrowed on wood which is several years old.

*Crotch angles.*—Primary branches are considered variable between about 46 to 55 degrees from the horizontal axis. This characteristic is not considered distinctive of the variety, however.

*Current season shoots.*—Surface texture — Substantially glabrous.

*Internode length.*—Approximately 2.4 to 2.6 cm.

*Color of mature branches.*—Medium brown, (RHS Greyed Orange Group 177 B).

*Current season shoots.*—Color — Light green, (RHS Yellow Green Group 152 B). The color of new shoot tips is considered a bright and shiny green (RHS Green Group 141 C).

Leaves:

*Size.*—Considered medium large for the species. Leaf measurements have been taken from vigorous, upright, current-season growth at approximately mid-shoot.

*Leaf length.*—Approximately 158.0 to about 172.0 millimeters.

*Leaf width.*—Approximately 35.0 to about 42.0 millimeters.

*Leaf base shape.*—Slightly oblique relative to the leaf longitudinal axis.

*Leaf form.*—Lancelolate.

*Leaf tip form.*—Acuminate.

*Leaf color.*—Dark green, (approximately RHS Green Group 139 A).

*Leaf texture.*—Glabrous.

*Lower surface.*—Medium green, (RHS Yellow Green Group 147 B).

*Leaf venation.*—Pinnately veined.

*Mid-vein.*—Color — Light yellow green, (RHS Yellow Green Group 151 A).

*Leaf margins.*—Slightly undulating. Form — Considered crenate, occasionally doubly crenate. Uniformity — Considered generally uniform.

*Leaf petioles.*—Size — Considered medium. Length — 9.0 to about 12.5 mm. Diameter — 1.5 to about 2.0 mm. Color — Green, (RHS Green Group 139 A).

*Leaf glands.*—Size — About 1.0 mm in height and about 1.0 mm in width. Number — Generally one per side, occasionally two per side. Type — Globose, and considered reasonably unappressed relative to the petiole margin. Color — Yellow-brown, (RHS Yellow Green Group153 B).

*Leaf stipules.*—Size — Considered medium-large for the variety. Number — Typically 2 per leaf bud, and up to 6 per shoot tip. Form — Lanceolate in form, and having a serrated margin. Color — Green, (RHS Green Group 139 B) when young, but graduating to a brown color, (RHS Greyed Orange group N167 A) with advancing senescence. The stipules are considered to be early deciduous.

Flowers:

*Flower buds.*—Generally — The floral buds, depending upon the stage of development, are typically approximately 6.0 millimeters wide; about 10.0 millimeters long; conic in form; and slightly appressed relative to the bearing shoot.

*Flower buds.*—Color — Dependent upon the proximity to bloom. The bud scales are reddish-brown, (approximately RHS Greyed Purple Group 183 D). The flower buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Mar. 1, 2002.

*Blooming time.*—Considered mid-season in relative comparison to other commercial peach cultivars grown in the central San Joaquin Valley. Date of full bloom was observed on Mar. 7, 2002. The date of bloom varies slightly with climatic conditions and cultural practices.

*Duration of bloom.*—Approximately 9 days. This characteristic varies slightly with the prevailing climatic conditions.

*Flower type.*—The variety is considered to have a showy type flower.

*Flower size.*—Flower diameter at full bloom is approximately 40.0 to 45.0 millimeters.

*Bloom quantity.*—Considered abundant.

*Flower bud frequency.*—Normally 1 to 2 appear per node.

*Petal size.*—Generally — Considered medium-large for the species. Length — Approximately 18.0 to about 20.0 millimeters. Width — Approximately 17.0 to about 19.0 millimeters.

*Petal form.*—Broadly rotund.

*Petal count.*—Nearly always 5. Occasionally inferior double petals are present.

*Petal texture.*—Glabrous.

*Petal color.*—Light pink, (RHS Red Purple Group 68 D) and darkening to a medium pink, (RHS Red Purple Group 68 C).

*Fragrance.*—Slight.

*Petal claw.*—Form — The claw is considered truncate, and has a medium-small size when compared to other varieties. Length — Approximately 6.0 to about 8.0 millimeters. Width — Approximately 5.0 to about 6.0 millimeters.

*Petal margins.*—Generally considered variable, from nearly smooth to slightly ruffled, to occasionally moderately undulate.

*Petal apex.*—Generally — The petal apices generally appear slightly grooved at the tip.

*Flower pedicel.*—Length — Considered medium-long, and having an average length of approximately 3.0 to about 4.0 millimeters. Diameter — Considered average, approximately 2.0 millimeters. Color — A medium brown, (RHS Greyed Orange Group N167 D).

*Floral nectaries.*—Color — A Dull orange, (RHS Greyed Orange Group 174 B).

*Calyx.*—Surface Texture — Generally glabrous. Color — A dull red, (approximately RHS Greyed Purple Group 183 D).

*Sepals.*—Surface Texture — The surface has a short, fine pubescent texture. Size — Average, and ovate in form. Color — A dull red, (approximately RHS Greyed Red Group 183 D).

*Anthers.*—Generally — Average to above average in length. Color — Red to reddish-orange dorsally, (approximately RHS Greyed Red Group 181 A).

*Pollen production.*—Pollen is abundant, and has a yellow color, (approximately RHS Yellow Orange Group 17 B).

*Filaments.*—Size — Variable in length, and considered medium short. Approximately 12.0 to 16.0 millimeters. Color — Considered a pinkish-white, (RHS Red Purple Group 62 D).

*Pistil.*—Number — Usually 1, rarely 2. Generally — Average in size. Length — Approximately 16.0 to about 19.0 millimeters including the ovary. Color — Considered a very pale green, (approximately RHS Yellow Green Group 150 D). Surface Texture — The variety has a long pubescent pistil.

Fruit:

*Maturity when described.*—Firm ripe condition (shipping ripe). Date of first picking — Jun. 8, 2002. Date of last picking — Jun. 17, 2002. The date of harvest varies slightly with the prevailing climatic conditions.

*Size.*—Generally — Considered large, and uniform. Fruit size can be influenced by cultural practices.

*Average cheek diameter.*—Approximately 79.0 to about 85.0 millimeters.

*Average axial diameter.*—Approximately 77.0 to about 80.0 millimeters.

*Typical weight.*—Approximately 348.0 grams. This characteristic is highly dependent upon cultural practices and therefore is not distinctive of the variety.

*Fruit form.*—Generally — Moderately oblate. The fruit is generally uniform in symmetry.

*Fruit suture.*—Shallow and extending from the base to apex. No apparent callousing or stitching exists along the suture line.

*Suture.*—Color — This has a yellow background color, (approximately RHS Yellow Group 8 B) and occasionally having some additional red orange coloration, (approximately RHS Orange Red Group N34 B).

*Ventral surface.*—Form — Slightly indented.

*Apex.*—Rounded. Occasionally small tips are observed.

*Base.*—Generally retuse.

*Stem cavity.*—Rounded to slightly elongated in the suture plane. Average depth of the stem cavity is about 1.3 cm. Average width is about 2.2 cm.

*Fruit skin.*—Thickness — Considered medium in thickness, and tenacious to the flesh. Texture — Short, fine and pubescent. Taste — Non-astringent. Tendency to crack — None observed.

*Color.*—Blush Color — This red blush color is variable from a reddish orange, (approximately RHS Orange Red Group N34 B), to a dark red, (approximately RHS Orange Red Group 34 A). Blush color ranges from about 75% to about 90% of the fruit surface depending upon the amount of sunlight exposure, and the prevailing growing conditions. Ground Color — Yellow orange, (approximately RHS Yellow Group 8 B).

*Fruit stem.*—Medium in length, approximately 6.0 to about 9.0 millimeters. Diameter — Approximately 2.0 to about 3.0 millimeters. Color — A pale yellow-green, (approximately RHS Yellow Green Group 145 C).

*Flesh.*—Ripening — Considered even. Texture — Firm, and dense. The flesh is considered non-melting. Fibers — A few, small, and tender ones are found. Aroma — Very slight. Eating Quality — Very good. Flavor — Considered sweet, and mildly acidic. The flavor is considered both pleasant and balanced. Juice — Moderate. Brix — About 15.0 degrees. This characteristic varies slightly with the number of fruit per tree, the prevailing cultural practices, and the surrounding climatic conditions. Flesh Color — Pale yellow, (approximately RHS Yellow Orange Group 16 C).

Stone:

*Type.*—Clingstone.

*Size.*—Considered medium-large for the variety. The stone size varies significantly depending upon the tree vigor, crop load and the prevailing growing conditions.

*Length.*—Average, about 27.0 to about 32.0 millimeters.

*Width.*—Average, about 24.0 to about 28.0 millimeters.

*Diameter.*—Average, about 17.0 to about 19.0 millimeters.

*Form.*—Obovoid.

*Base.*—The stone is usually rounded to slightly oblique relative to the ventral side.

*Apex.*—Shape — The stone apex is raised and is reasonably prominent.

*Stone surface.*—Surface Texture — Irregularly furrowed toward the dorsal side. Pitting is abundant generally, and is typically more noted than furrowing. Ridges — The surface texture varies from sharp to rounded. Ventral Edge — Width — Considered medium, and having a dimension of approximately 3.0 to 5.0 millimeters when measured at the mid-suture. Dorsal Edge — Shape — Full, heavily grooved, and having jagged edges basally.

*Stone color.*—The color of the dry stone is a light orange, (approximately RHS Orange Group 26 D).

*Tendency to split.*—Splitting occurs only rarely.

*Kernel.*—Size — Kernel is considered medium large. Form — Considered ovoid. Pellicle — Pubescence is not developed at fruit senescence. Color — Approximately RHS Greyed Orange Group 167 B.

*Use.*—The subject variety 'Burpeachsixteen' is considered to be a early mid-season maturing Peach tree, which produces fruit that are considered firm, attractively colored, and which are useful for both local and long distance shipping.

*Keeping quality.*—Excellent. Fruit has stored well up to 25 days after harvest at 1.0 degree Celsius.

*Shipping quality.*—Considered good. Fruit showed minimal bruising of flesh or skin damage after being subjected to normal harvesting and packing procedures.

*Resistance to insects and disease.*—No particular susceptibilities were noted. The present variety has not been tested to expose or detect any susceptibilities or resistances to any known plant and/or other fruit diseases.

Although the new variety of peach tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety peach tree, what we claim is new and desire to secure by Plant Letters Patent is:

1. A new distinct variety of peach tree substantially as illustrated and described, and which is characterized principally as to novelty by producing an attractively colored yellow-fleshed, clingstone peach which is mature for harvesting and shipment approximately June 8 to June 15 under the ecological conditions prevailing in the San Joaquin Valley of central California.

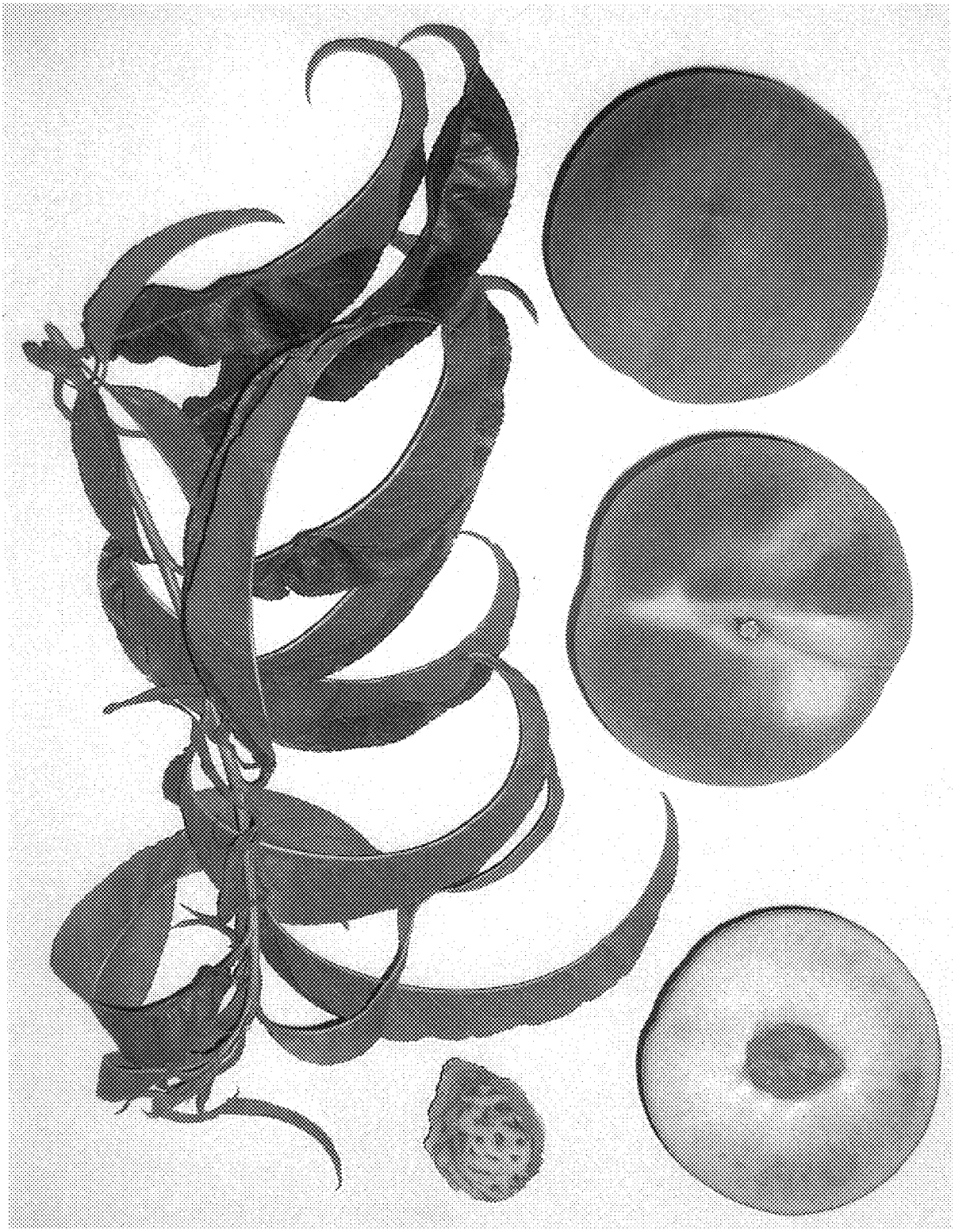

* * * * *